United States Patent [19]

Evans

[11] Patent Number: 4,519,245

[45] Date of Patent: May 28, 1985

[54] METHOD AND APPARATUS FOR THE NON-DESTRUCTIVE TESTING OF MATERIALS

[76] Inventor: Herbert M. Evans, R.D. #1, Box 231, Spring City, Pa. 19475

[21] Appl. No.: 482,149

[22] Filed: Apr. 5, 1983

[51] Int. Cl.³ ............................................ G01N 29/00
[52] U.S. Cl. ...................................... 73/579; 73/573; 73/588
[58] Field of Search .......................... 73/579, 573, 588

[56] References Cited

U.S. PATENT DOCUMENTS

| | | | |
|---|---|---|---|
| 3,580,056 | 5/1971 | Warner | 73/579 |
| 4,128,011 | 12/1978 | Savage | 73/579 |
| 4,281,547 | 8/1981 | Hinshaw et al. | 73/579 |
| 4,342,229 | 8/1982 | Massa | 73/579 |
| 4,400,980 | 8/1983 | Lepert | 73/665 |
| 4,479,386 | 10/1984 | Beggs et al. | 73/582 |

Primary Examiner—Howard A. Birmiel
Attorney, Agent, or Firm—Robert J. Mooney

[57] ABSTRACT

A method and apparatus for the non-destructive testing of materials, particularly composite structures and other such laminated materials, which comprises repeatedly impacting the material being tested with a precisely regulated force having a pre-determined magnitude. The response generated by the material is detected by a sensor and a proportional electrical signal is generated. The electrical signal is compared with a stored electrical signal previously generated in response to impacting a defect-free reference material with the same precisely regulated pre-determined force. A difference in frequency and amplitude between the two compared electrical signals is indicative of a defect in the material being tested.

16 Claims, 5 Drawing Figures

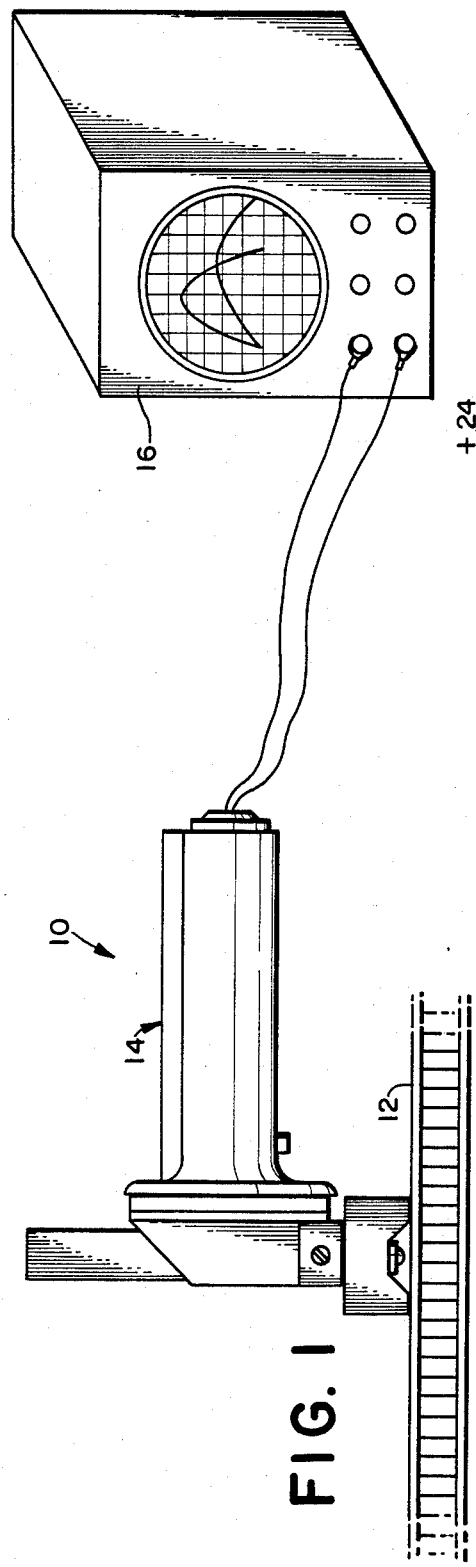
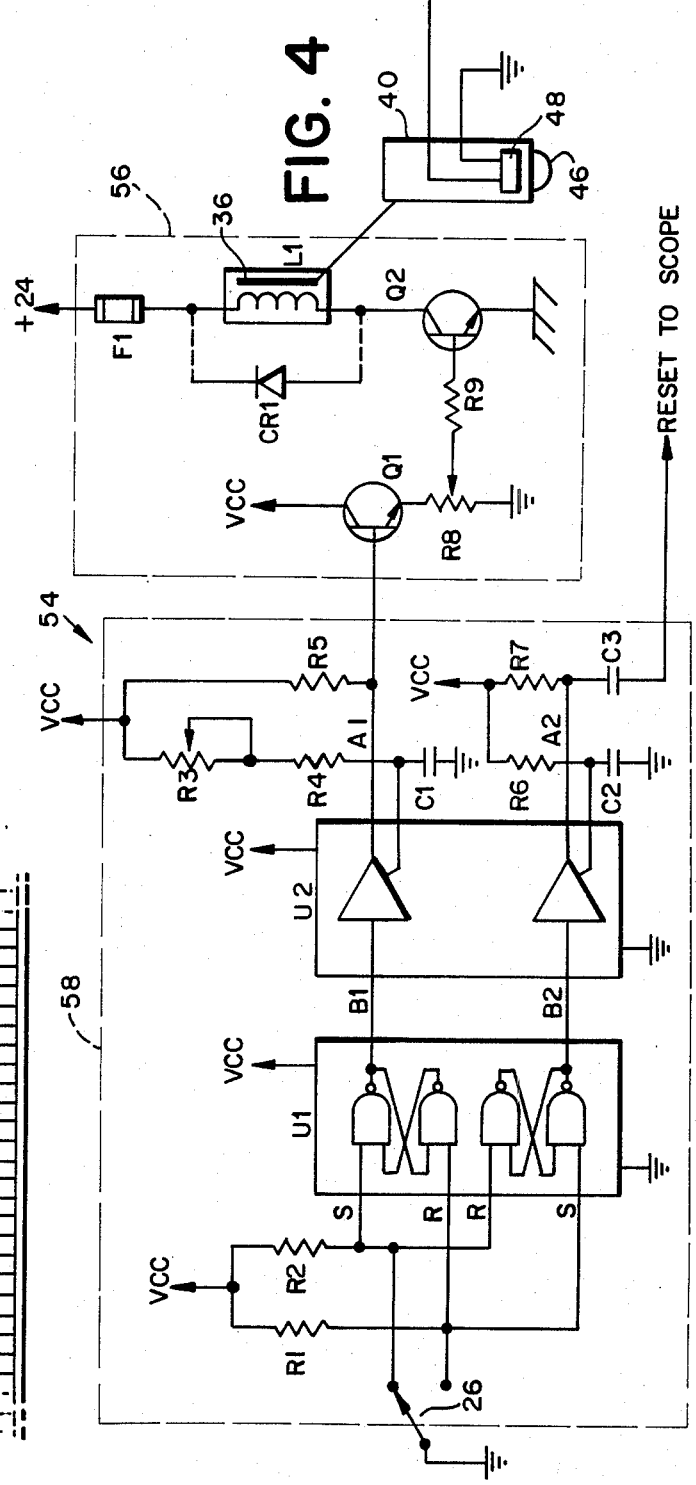
FIG. 1
FIG. 4

METHOD AND APPARATUS FOR THE NON-DESTRUCTIVE TESTING OF MATERIALS

BACKGROUND OF THE INVENTION

The present invention relates generally to a method and apparatus for the non-destructive testing of materials and, more particularly to such a method and apparatus which may be employed to detect delaminations, debonds and other such imperfections or defects in composite structures or similar laminated materials and the like.

Several prior art methods are presently employed for the non-destructive testing or inspection of materials such as composite structures and other such laminated materials. The testing or inspection of such composite structures is required in order to determine whether any defects or imperfections occurred or developed during initial formation as well as to determine whether any such defects or imperfections have subsequently developed within such composite structures either as a result of operational usage or due to some other external cause such as a known or unknown impact. Such defects or imperfections may include, for example delaminations, debonds, voids in the bonds between materials, and the like. In many cases it is important that such defects or imperfections be discovered and remedied, particularly in certain critical applications such as, for example, where the composite structure is employed as a stabilizer on an expensive, high performance airplane.

The oldest and simplest method of non-destructively testing or inspecting such composite structures is the so-called tap test or coin tap test. In this method the surface of the composite structure is lightly tapped or struck repeatedly at different locations with a suitable solid object such as a coin, bolt or ball bearing. The audible response or reflection from the various "taps" are then subjectively evaluated by the person performing the test in order to detect a change of pitch or lower frequency response. The areas in which a lower frequency response is encountered are the areas in which a defect or imperfection is present. Although, this technique has proven to be a very practical means of non-destructive testing it is somewhat imprecise due to its highly subjective nature and reliance upon the human ear.

Other methods of non-destructive testing or inspection employ radiography (X-rays, gamma rays or neutron transmissions), ultrasonics, or thermal detection techniques. Although these prior art methods have achieved some success in certain applications they all utilize rather sophisticated equipment which is relatively expensive to obtain and operate. These more sophisticated techniques also generally require a highly trained operator to control the equipment and to interpret the results. In addition some of these techniques may require a special coupling or special surface preparation and/or a controlled operating environment, thereby rendering them generally unsuitable for operation in the field. Moreover, some of these techniques are only useful for testing or inspecting materials having a limited thickness.

The present invention overcomes these and many other disadvantages by providing a relatively simple, real-time method and apparatus for non-destructive testing of composite materials which is relatively unaffected by the operating environment and the internal geometry or thickness changes in the material being tested. The present invention requires no special coupling or surface preparation and permits the extent of the area of the defects or imperfections within the material to be objectively determined and accurately mapped. The present invention is particularly well suited for remote or field use due to its structural and operational simplicity.

SUMMARY OF THE INVENTION

Briefly stated, the present invention comprises a method and apparatus for the non-destructive testing of materials, particularly composite structures or other such laminated materials. The method involves impacting the surface of a reference material known to be free of defects with a predetermined force. The response from the reference material is detected and a proportional electrical signal is generated and stored. Thereafter, the surface of the material being tested is impacted with the same predetermined force. The response from the material being tested is also detected and a proportional electrical signal is generated. The two electrical signals are compared to determine the presence of an amplitude and/or a frequency difference which is indicative of a defect in the material being tested. The apparatus comprises an impactor means for impacting the surface of the material with the predetermined force and control means for controlling the operation of the impactor means. Sensor means are included for detecting the response to the impact and for generating the proportional electrical signal. Comparison means (in the preferred embodiment, a storage oscilloscope) is provided to receive the electrical signal and compare it to the stored electrical reference signal.

BRIEF DESCRIPTION OF THE DRAWINGS

The foregoing summary, as well as the following detailed description of a preferred embodiment of the present invention will be better understood when read in conjunction with the appended drawings, in which:

FIG. 1 is a perspective view of a non-destructive testing apparatus in accordance with the present invention;

FIG. 4 is a schematic circuitry diagram of the control portion of the apparatus of FIG. 1.

DESCRIPTION OF A PREFERRED EMBODIMENT

Figure 2:
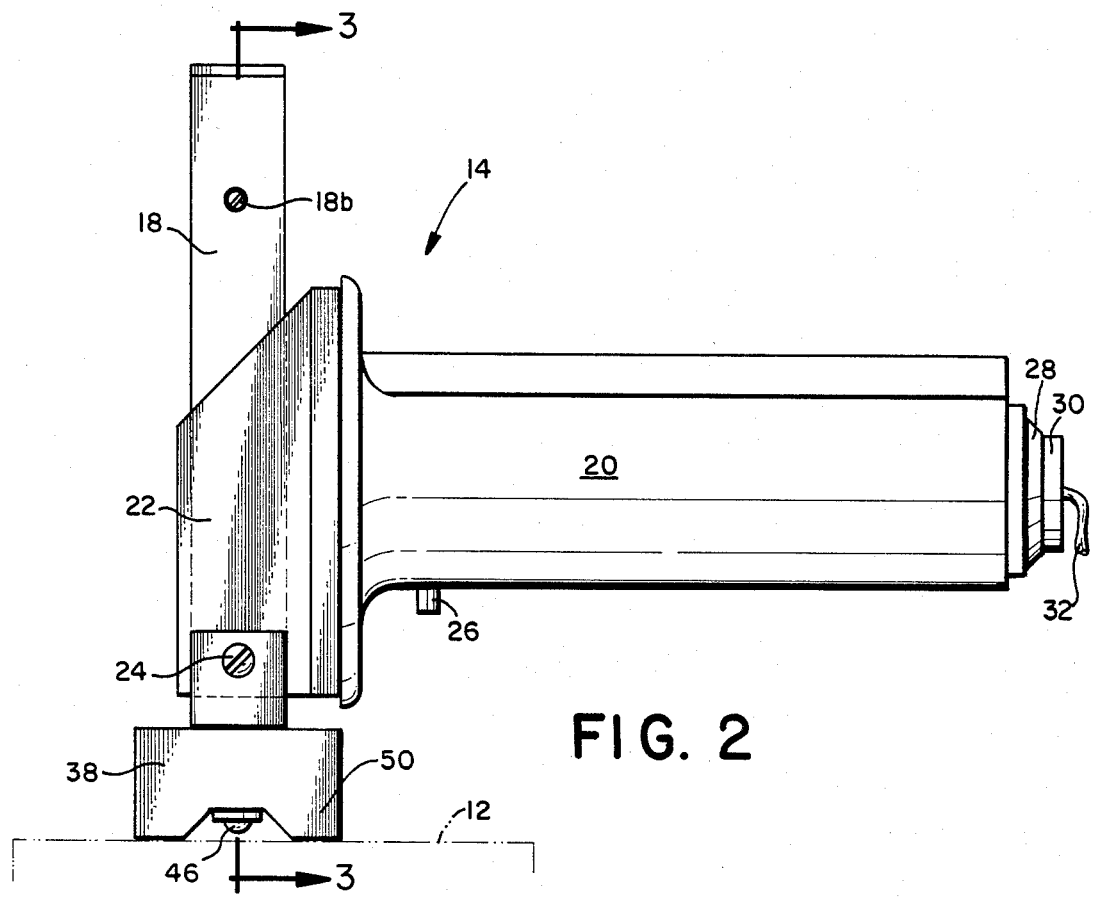
FIG. 2 is an enlarged side elevation view of the impactor portion of the apparatus of FIG. 1.

Referring to the drawings and particularly to FIG. 1 there is shown an apparatus, generally 10, for the non-destructive testing or inspection (hereinafter jointly referred to as "testing") of a material 12, particularly a composite structure or other such laminated material or the like (hereinafter collectively referred to as a "composite material" or composite structure"). The apparatus 10 as shown comprises four major subassemblies; an impactor means or impactor, (shown generally as 14) for impacting the surface of the composite structure with a predetermined force; control means (not shown on FIG. 1) for precisely regulating the operation of the impactor (in a manner hereinafter described in connection with FIG. 4); sensor means (also not shown on FIG. 1) for detecting the response from the material subsequent to its being impacted by the impactor means 14 and for generating an electrical signal proportional to the amplitude and frequency of the response (as hereinafter described in connection with FIGS. 2, 3 and 4); and comparison means, in the present embodiment a storage oscilloscope 16 for receiving and displaying the electrical signal from the sensor means along with a stored reference signal for comparison therewith. It will be appreciated that while a storage oscilloscope 16 is employed as a visual comparison means in the present embodiment, the invention is not limited to such a comparison means.

In operation, the impactor means 14 is first employed to impact the surface of a reference sample of the composite material which is known to be substantially free of any defects, imperfections or the like (hereinafter collectively referred to as "defects"). The impact to the surface of the reference material is made with a predetermined force. The response from the reference sample is detected by the impactor in a manner hereinafter described and a first or reference electrical signal proportional to the response is generated and stored within the storage oscilloscope 16. Thereafter the surface of the material 12 being tested is impacted by the impactor means 14 with the same precisely regulated predetermined force at a first test location. Again, the response from the material 11 is detected and second electrical signal proportional to the response is generated. The second electrical signal is also supplied to the oscilloscope. The two electrical signals are then simultaneously displayed on the oscilloscope for visual comparison.

The comparison between the two electrical signals is done primarily on the basis of frequency and amplitude. A defect in a composite structure causes a change in the frequency and amplitude of the response to a surface impact, from the response which would otherwise be emitted by a composite structure which is free from any such defects. Generally the frequency and amplitude of the response from a composite structure having a defect is lower than that of the defect free or reference response. By simultaneously displaying the first or reference signal, indicative of the expected response if no efects are present in the composite structure, and the second or test signal, the two signals can be visually compared and any substantial frequency shift and/or decrease of amplitude can be readily ascertained.

Once such a defect is encountered at a particular test position, the impactor means 14 may be moved to other test positions around the surface of the material being tested in a predetermined course or pattern, performing a test and comparison at each such position. The predetermined pattern may comprise a relatively simple straight line pattern, a radial pattern or the like depending upon the particular application. By performing a series of such tests in this manner the full extent of a detected defect in the composite structure may be quickly and conveniently determined and accurately mapped. Thereafter the results of the testing may be evaluated and the defective portion of the composite structure may be repaired or replaced as required.

Figure 3:
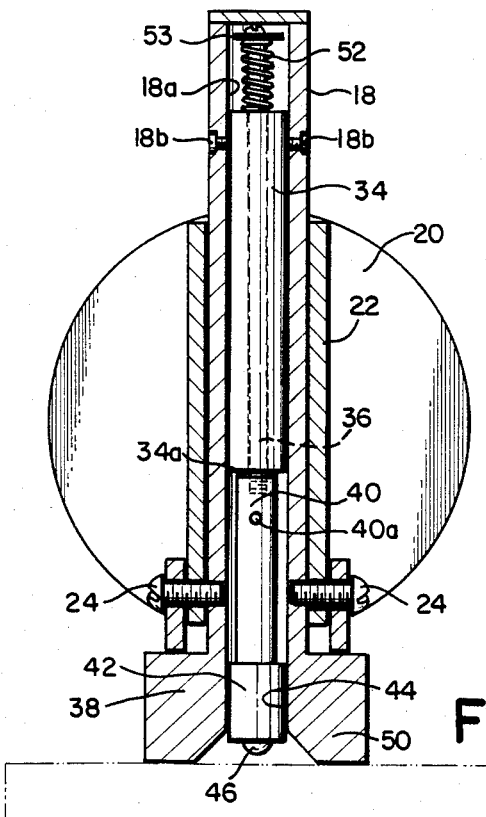
FIG. 3 is a sectional view of the impactor of FIG. 2 taken along section line 3—3.

Referring now to FIGS. 2 and 3 there is shown more detailed views of the impactor 14. The impactor 14 comprises an elongated, generally rectangular solenoid housing 18 shown on FIGS. 2 and 3 as being generally vertically oriented. A suitable handle 20 is attached to the solenoid housing 18 for the convenience of the operator. The handle 20 is generally cylindrical and is suitably sized to accommodate the natural grip of an operator. The end of the handle 20 which abuts the solenoid housing 18 includes a bracket 22 which surrounds a portion of the solenoid housing 18 and is attached thereto with screws 24. For purposes which will hereinafter become apparent, the handle 20 further includes a push button switch 26 on the lower portion thereof proximate to the solenoid housing 18. The distal end of the handle 20 includes a conventional electrical connector 28 which is attached to a complimentary or mating connector 30 and a suitable multi-conductor electrical cable 32 for electrically inter-connecting the impactor 14 and the storage oscilloscope 16 (shown only on FIG. 1).

Referring now to FIG. 3, there is shown a sectional view of the rectangular solenoid housing 18. Positioned within a cylindrical blind bore 18a and fixedly attached to the solenoid housing 18 with set screws 18b is a conventional cylindrically shaped solenoid 34. The solenoid 34 includes a conventional actuating coil (not shown on FIG. 3) and a plunger 36. In the present embodiment, the solenoid 34 is positioned and oriented so that when an appropriate electrical current is passed through the actuating solenoid coil, the plunger 36 is impelled toward the base 38 of the solenoid housing 18, downwardly as shown on FIG. 3.

Also positioned within the solenoid housing 18 is a generally cylindrical tap hammer 40. The tap hammer 40 is threadably coupled to the solenoid plunger 36 for translational movement therewith. The coupling between the plunger 36 and the tap hammer 40 is adjustable. The lower end of the tap hammer 40 includes a metallic collar 42 having a diameter slightly larger than the diameter of the upper portion of the tap hammer 40. The collar 42 is positioned within a generally cylindrical opening 44 which extends through the solenoid housing base 38. The inside diameter of the opening 44 is slightly greater than the outside diameter of the collar 42 to permit the opening 44 to facilitate and keep in alignment the reciprocating movement of the collar 42. Attached to the lower end of the collar 42 is a generally semispherically shaped impactor tip 46. The impactor tip 46 is constructed of a relatively hard material such as steel and is the part of the impactor 14 which actually impacts or taps the surface of the material being tested.

Figure 3A:
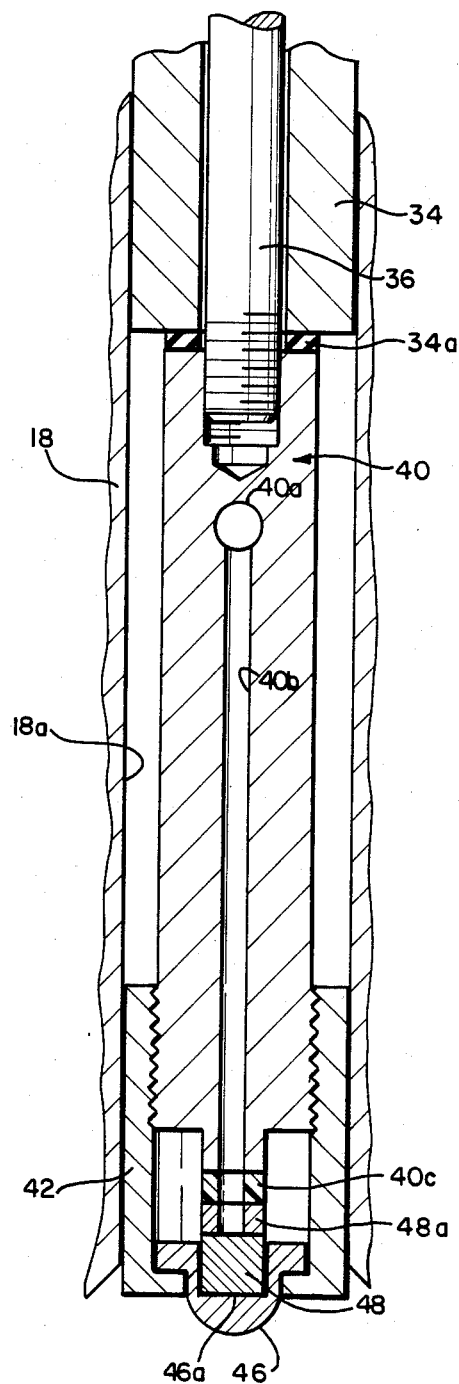
FIG. 3A is an enlarged fragmented sectional view of the lower end of the impactor of FIG. 2 also taken along section line 3—3.

An enlarged fragmented sectional view of the lower end of the impactor shown in FIG. 2, taken along section line 3—3, is shown in FIG. 3A to further illustrate the arrangement of the major working element of the impactor. The movable plunger 36 is threadably and adjustably secured to the tap hammer 40. A rubber O-ring 34a is secured to the lower end of the solenoid 34 and serves to cushion mechanical shock between the tap hammer 40 and the solenoid 34. The tap hammer 40 is a solid block of metal, preferrably aluminum, having a transverse bore 40a and an axial bore 40b extending from the transverse bore 40a to the lower end of the tap hammer 40.

The lower end of the tap hammer 40 has a reduced diameter portion to which a teflon insulator 40c is secured. The teflon insulator 40c abuts a brass contact plate 48a abutting a transducer 48. The transducer 48 reposes within a recess 46a formed in the flanged impactor tip 46. The impactor tip 46 is captured and held against the transducer 48 as the flanged collar 42 is threadably secured to the tap hammer 40.

Not shown for clarity's sake are the two signal wires which extend from the handle 20 through the transverse bore 40a where or near one of the wires is grounded and where the other wire extends down through the axial bore 40b to make connection with the contact plate 48a which is in electrical connection with the transducer 48. The transducer 48 is a conventional piezo-electric device which is mechanically coupled to the impactor tip 46 so that impacts experienced by the tip 46 are imparted to the transducer 48. The transducer 48 produces an electrical signal proportional to the extent and rate of compression experienced by the impactor tip 46 as the impactor tip 46 impacts the surface of the material being tested. Suitable wiring (not shown) extends between the transducer 48 and the handle connector 28 to permit the transmission of electrical signals generated by the transducer 48 to the storage oscilloscope 16 (shown on FIG. 1 only).

A coil spring 52 is located within the solenoid housing 18. The lower end of the spring 52 abuts the top of the stationary solenoid 34 and the upper end abuts a washer 53 secured to the reciprocable plunger 36. During assembly or recalibration the threaded coupling between the tap hammer 40 and the solenoid 34 is adjusted to the point where the coil spring 52 is at the onset of compression. When the solenoid 34 is activated the plunger moves downwardly and the spring is compressed between the washer 53 and the stationary solenoid 34. When the solenoid 34 is deactivated, the then compressed spring 52 returns the plunger 36 and the attached impactor tip 46 to the initial position shown in FIG. 3, a position at which the impactor tip 46 is situated a predetermined distance from the surface of the material 12 to be tested.

The base 38 solenoid housing 18 includes four legs 50 which extend outwardly therefrom. The legs 50 are suitably sized and shaped to aid the maintenance of a predetermined distance between the impactor tip 46 and the surface of the material 12 to be tested. A preferred predetermined distance is 0.100 inch but the predetermined distance may be altered by loosening the set screws 18b and altering the position of the solenoid 34 and those elements attached to it.

The legs 50 serve to provide a stable four point contact between the impactor 14 and the surface of the composite material being tested. Additionally, the legs 50 cooperate with the base opening 44 and the collar 42 to insure that the downward movement of the impactor tip 46 is substantially perpendicular to the surface of the composite material at the position being tested. In the present embodiment the legs 50 are flat surfaced. However, if the composite structure being tested has other than a flat surface, for example, a curved surface, suitable shaped legs (not shown) which conform to the surface of the material being tested may be substituted for the legs 50 as shown in order to maintain the predetermined spacing and substantially perpendicular relationship between the impactor tip 46 and the point of impact on the surface of the material to be tested.

In the operation of the impactor 14, the solenoid plunger 36, the tap hammer 40, the collar 42 and the impactor tip 46 are all maintained by the spring 52 in their initial, unactivated position as shown on FIG. 3. When the impactor 14 is properly positioned with all four legs 50 fully contacting the surface of the composite material to be tested, the push button switch 26 is depressed by the operator. Reacting to the momentary activation of the switch 26, the control means 54 (shown in FIG. 4) permits a precisely regulated amount of electrical current to activate the solenoid coil (not shown of FIG. 3). The precisely controlled flow of current through the solenoid coil generates a precise and repeatable downwardly directed force on the plunger 36 and causes the plunger 36 and the attached tap hammer 40, collar 42 and impactor tip 46 to move downwardly, thereby causing the impactor tip 46 to strike the surface of the material being tested with substantially the same predetermined force each time the solenoid coil is activated. The transducer 48 operates to generate an electrical signal proportional to the impact in the manner described above. Thereafter, the control means 54 prevents further current from flowing through the solenoid coil (not shown on FIG. 3) and the spring 52 restores the plunger 36 and the attached tap hammer 40, collar 42 and the impactor tip 46 back to their initial starting positions as shown on FIG. 3.

Referring now to FIG. 4, there is shown a schematic diagram of the control means 54 of the present embodiment. The control means 54 is physically positioned within the impactor handle 20 (FIG. 2) but could be installed outside of the impactor 14 if desired. The control means is comprised of two main sections: a solenoid current regulator and trigger section 56 and a timing and reset section 58.

The timing and reset section 58 is comprised of two integrated circuits U1 and U2 and their associated biasing and control circuitry. Integrated circuit U1 is a conventional latch circuit internally comprised of two set-reset Flip-Flops each having their RESET terminals respectively connected to the other's SET terminals to produce outputs which are exactly 180 degrees out of phase.

The SET terminal of the first Flip-Flop and the RESET terminal of the second Flip-Flop are connected to voltage VCC through biasing resistor R2 and are also connected to ground through the normally closed pole of the momentary switch 26. Similarly, the SET terminal of the second Flip-Flop and the RESET terminal of the first Flip-Flop are connected to VCC through biasing resistor R1 and are also connected to the normally open pole of switch 26. When the circuit is in the unactuated state (switch 26 in the normally closed position) as shown on FIG. 4, the first Flip-Flop is in the set condition with its output B1 sitting high and the second Flip-Flop is in the reset condition with its output B2 sitting low. When the momentary switch 26 is depressed by the operator, the arm of the switch momentarily connects the RESET terminal of the first Flip-Flop and the SET terminal of the second Flip-Flop to ground causing both Flip-Flops to reverse condition which causes the output B1 of the first Flip-Flop to go low and the output B2 of the second Flip-Flop to go high. Thereafter both Flip-Flops reverse condition and reassume their initial condition as shown. In this manner, integrated circuit U1 also functions as a debounce circuit to isolate the momentary switch 26 from the reset of the circuitry.

The output terminal of each of the Flip-Flops within integrated circuit U1 are connected directly to the input terminals of integrated circuit U2. Integrated circuit U2 is a conventional dual timer circuit and is commercially available from National Semiconductor Corporation under model number NE 558A. Each of the two internal timers within integrated circuit U2 are configured as a standard one-shot to provide a high on their respective output terminals A1, A2 upon the receipt of a negative going pulse (low) on its input terminal.

The outputs A1, A2 from the timers will remain high for that period of time established by the particular R-C time constant. In the case of the first timer, the R-C timer circuit is comprised of capacitor C1 and series resistors R3 and R4. Resistor R3 is variable to permit the output from the first timer to remain high for an operator controlled time period for purposes which will hereinafter become apparent. The R-C timer circuit for the second timer is comprised of capacitor C2 and resistor R6. The time period of the second timer is fixed. Biasing resistors R5 and R7 are respectively connected to the timer output terminals.

The output terminal A2 of the second timer is connected through coupling capacitor C3 to the sweep control of the storage oscilloscope 16. The second timer acts as a one-shot and upon receipt of a negative going pulse from the second Flip-Flop within integrated circuit U2 produces a reset pulse which continues for a fixed duration in accordance with the fixed time constant of its RC timer circuit (R6 and C2). The oscilloscope 16 is re-armed upon the receipt of each such reset pulse. If desired the reset pulse may be delayed by conventional means to prevent a new sweep until the impactor 46 has returned to its initial position.

The current regulator and trigger section 56 comprises two transistors Q1 and Q2 and their associate circuitry. The output terminal A1 of the first timer of integrated circuit U2 is connected directly to the base of transistor Q1. Transistor Q1 is connected in an emitter-follower configuration with its collector connected directly to VCC and its emitter connected to ground through variable resistor R8. In this configuration, transistor Q1 functions as a gated variable voltage source to provide an output of a duration determined by the duration of the high output pulse from the first timer. The output of the emitter-follower circuit Q1 is taken off the wiper of variable resistor R8 to provide an adjustable driving potential which is connected through current limiting resistor R9 to the base of transistor Q2. Thus, the output of the emitter-follower circuit can be varied or controlled in both magnitude and duration.

Transistor Q2 is connected as a gated constant current sink. The emitter of transistor Q2 is connected directly to ground and its collector is connected through the solenoid coil L1 to a driving potential voltage source appropriate for actuating the solenoid, in the present embodiment a 24 volt source. An inline fuse F1 may be employed for safety reasons and a diode CR1 is connected across the solenoid coil L1 to protect transistor Q2 from the reverse surge voltage of the inductance of the solenoid coil L1.

When a gated pulse is received from transistor Q1, transistor Q2 becomes conductive to allow a precise pulse of current to flow from the driving potential voltage source through the solenoid coil L1 to actuate the solenoid plunger 36. The duration of the current pulse flowing through the solenoid coil L1 and through transistor Q2 is determined by the time duration of the output pulse of the first timer which, as previously described, may be controlled by variable resistor R3. The magnitude of the current pulse flowing through the solenoid coil L1 and transistor Q2 is determined by the DC resistance of coil L1 and the resistance of the collector emitter junction. As previously described, the potential of the pulse applied to the base of transistor Q2 is controlled by variable resistor R8. Of course, as previously described, the force and duration of the movement of the solenoid plunger 36 as well as the impact imparted by the impactor tip 46 are directly controlled by the magnitude and duration of the current pulse flowing through the solenoid coil L1.

In operation, both the duration and magnitude of the solenoid coil current pulse are initially adjusted (by adjusting R3 and R8) for the particular type and thickness of the composite material being tested to provide an impact from the impactor 14 which is suitable for subsequent comparison i.e. the impact must be of a magnitude and duration sufficient to produce a measurable response. Hence, when the operator depresses the momentary action switch 26, the first Flip-Flop develops a negative going output pulse. Upon receipt of the negative going pulse, the first timer generates a high output pulse which continues for the period of time established by its R-C timing circuit. The pulse from the first timer causes the emitter-follower transistor Q1 to conduct and a positive pulse is applied to the base of Q2. As previously described the pulse applied to the base of transistor Q2 causes the actuation of the solenoid 34.

Once the two variable resistors R3 and R8 are initially set, the current pulse flowing through the solenoid coil L1 will have virtually the same magnitude and duration every time the momentary action switch 26 is depressed. Thus, as long as the impactor tip 46 is returned by the spring 52 (FIG. 3) to the same predetermined distance from the composite material subsequent to each impact, the force of each impact will be constant impact after impact. As is discussed above, it is necessary that the impactor force be of a constant magnitude and duration in order to be assured that the detected response from the material being tested is suitable for meaningful comparison with the stored reference signal.

From the foregoing description of a preferred embodiment and from the accompanying figures, it can be seen that the present invention provides a simple but effective method and apparatus for the real-time nondestructive testing of materials, particularly composite structures and other such laminated materials. It will be recognized by those skilled in the art that changes or modifications may be made to the above-described preferred embodiment without departing from the broad inventive concept of the invention. For example, instead of employing a storage oscilloscope to store and display the reference and test signals for visual comparison, the two signals may be converted to corresponding digital signals for storage and comparison in a suitable digital apparatus. It is understood, therefore, that the invention is not limited to the particular embodiment as shown and described, but it is intended to cover all changes and modifications which are within the scope and spirit of the invention as set forth in the appended claims.

I claim:

1. A method for the nondestructive testing of materials comprising the steps:
    a. impacting the surface of a reference sample of material known to be free of defects with a predetermined precisely regulated force of a variably controllable magnitude and duration;
    b. sensing the response from the reference sample and generating a first electrical signal proportional thereto;
    c. storing the generated first electrical signal;

d. impacting the surface of the material being tested at a first test location with the same predetermined, precisely regulated force as was applied in step a;

e. sensing the response from the material being tested and generating a second electrical signal proportional thereto; and f. comparing the first and second electrical signals to determine the presence of an amplitude and/or frequency difference there between, such amplitude and/or frequency difference indicating the existence of a defect in the material.

2. The method as recited in claim 1 and further comprising repeating steps d through f at other test locations on the surface of the material being tested to determine the extent of the defect in the material.

3. The method as recited in claim 2 wherein the test locations are selected in accordance with a predetermined pattern to provide a mapping of the extent of the defect in the material.

4. The method as recited in claim 1 and further comprising the step of displaying both the first and second electrical signals prior to step f to facilitate a visual comparison thereof.

5. An apparatus for the non-destructive testing of materials comprising:

impactor means for impacting the surface of the material with a predetermined force;

control means for precisely regulating the operation of the impactor means to adjust each of magnitude and duration of the force;

sensor means for detecting the response from the material subsequent to the material being impacted by the impactor means and for generating an electrical signal proportional to the amplitude and frequency of the detected response;

and comparison means for comparing the electrical signal from the sensor means with a stored reference signal to determine the presence of a difference in frequency or amplitude there between.

6. The apparatus as recited in claim 5 wherein the sensor means comprises a transducer coupled to the impactor means.

7. The apparatus as recited in claim 6 wherein the transducer comprises a piezo-electric device.

8. The apparatus as recited in claim 5 including display means for receiving and simultaneously displaying the electrical signal generated by the sensor means and the reference signal.

9. The apparatus as recited in claim 8 wherein the display means comprises a storage oscilloscope.

10. The apparatus as recited in claim 5 wherein the control means comprises solenoid means connected to the impactor means for the actuation thereof; and current regulator means connected to the solenoid means for precisely regulating the magnitude and duration of electrical current supplied to the solenoid means.

11. The apparatus as recited in claim 10 wherein the solenoid coil and the current regulator means includes a gated constant current sink connected in series with the solenoid coil.

12. The apparatus as recited in claim 11 wherein the current regulator means further comprises adjustable driving potential means connected to the base of the gated constant current sink for adjusting the voltage applied to the constant current sink to thereby adjust the current flowing through the solenoid coil.

13. The apparatus as recited in claim 12 wherein the adjustable driving potential means comprises an emitter-follower connected transistor in series with a variable resistor, the wiper of the variable resistor providing the connection to the base of the constant current sink.

14. The apparatus as recited in claim 13 wherein the current regulator means further includes timer means for controlling the on and off time of the emitter-follower connected transistor.

15. The apparatus as recited in claim 14 and further including switch means connected to the timer means for the activation of the timer means upon operation thereof by an operator.

16. An apparatus for the non destructive testing of material comprising:

a stationary solenoid, having a movable plunger and a coil, one end of the coil being connected to a current source and the other end being connected to a gated constant current sink;

a carrier adjustably secured to the plunger of the solenoid;

an impactor tip secured to the carrier;

a piezo-electric transducer, secured between the carrier and the impactor tip, having one side electrically insulated from the carrier;

a spring secured between the stationary solenoid and the movable plunger;

timer means for producing an electrical pulse having selectable amplitude and duration; and means for selectively triggering the timer means.

* * * * *